United States Patent [19]

Palfy

[11] Patent Number: 5,117,818
[45] Date of Patent: Jun. 2, 1992

[54] NASAL TUBE HOLDER

[76] Inventor: Christa U. Palfy, Lot 14, Kings Road, Marysville, Victoria 3779, Australia

[21] Appl. No.: 585,082
[22] PCT Filed: Mar. 10, 1989
[86] PCT No.: PCT/AU89/00096
 § 371 Date: Sep. 21, 1990
 § 102(e) Date: Sep. 21, 1990
[87] PCT Pub. No.: WO89/09043
 PCT Pub. Date: Oct. 5, 1989

[30] Foreign Application Priority Data
 Mar. 23, 1988 [AU] Australia ............................... PI7390
 Dec. 1, 1988 [AU] Australia ............................... PJ1788

[51] Int. Cl.⁵ ............................................. A61M 15/00
[52] U.S. Cl. ........................... 128/204.11; 128/207.18; 128/207.17; 128/DIG. 26; 128/200.24
[58] Field of Search ...................... 128/207.11, 207.13, 128/207.17, 207.18, 204.11, 206.21, DIG. 26, 200.24; 604/174, 179

[56] References Cited
U.S. PATENT DOCUMENTS

| | | | |
|---|---|---|---|
| 2,292,568 | 8/1942 | Kanter et al. ............... | 128/204.11 X |
| 2,831,487 | 4/1958 | Tafilaw . | |
| 2,868,199 | 1/1959 | Hudson ........................... | 128/207.18 |
| 3,161,199 | 12/1964 | Sands . | |
| 3,209,755 | 10/1965 | McCarthy . | |
| 3,648,703 | 3/1972 | Manker ........................... | 604/179 |
| 3,713,448 | 1/1973 | Arrott ..................... | 128/DIG. 26 X |
| 3,977,407 | 8/1976 | Coleman et al. ................. | 604/179 |
| 4,106,505 | 8/1978 | Salter et al. ..................... | 128/207.18 |
| 4,282,871 | 8/1981 | Chodorow et al. ............. | 128/207.18 |
| 4,284,076 | 8/1981 | Hall ................................. | 128/207.18 |
| 4,351,331 | 9/1982 | Gereg ............................. | 128/207.17 |
| 4,406,283 | 9/1983 | Bir ................................... | 128/207.18 |
| 4,465,067 | 8/1984 | Koch et al. ...................... | 128/207.18 |
| 4,480,639 | 11/1984 | Peterson et al. ................ | 128/207.18 |
| 4,559,941 | 12/1985 | Timmons et al. ............... | 128/207.18 |
| 4,572,177 | 2/1986 | Tiep et al. .................. | 128/207.18 X |
| 4,660,555 | 4/1987 | Payton ............................ | 128/207.18 |
| 4,739,757 | 4/1988 | Edwards ......................... | 128/207.18 |
| 4,753,233 | 6/1988 | Grimes ............................ | 128/207.18 |
| 4,808,160 | 2/1989 | Timmons et al. .......... | 128/207.18 X |

FOREIGN PATENT DOCUMENTS

| | | | |
|---|---|---|---|
| 98119 | 12/1987 | European Pat. Off. ............ | 604/174 |
| 28036 | 7/1884 | Fed. Rep. of Germany ......................... | 128/207.18 |
| 1124404 | 10/1951 | France ............................. | 128/207.18 |
| 247590 | 2/1940 | Sweden ........................... | 128/207.18 |
| 8703704 | 6/1987 | World Int. Prop. O. ....... | 128/207.18 |

Primary Examiner—Edgar S. Burr
Assistant Examiner—Eric Raciti
Attorney, Agent, or Firm—Baker & Daniels

[57] ABSTRACT

A nasal tube holder which provides a comfortable and close fitting holder assembly capable of use for reasonably long periods of time, the holder having head attachment loops made of a flexible material adapted to conform to a patient's face, the loops having central tube holder clip elements at a forward position adapted to be worn in close proximity to the patient's nose and further tube clip elements carried by the flexible loops for movement therealong so that a nasal tube can be clipped through the central tube holder clip elements and thereafter through one of the side tube holder clip elements with the side tube holder clip elements being movable to enhance patient comfort.

11 Claims, 7 Drawing Sheets

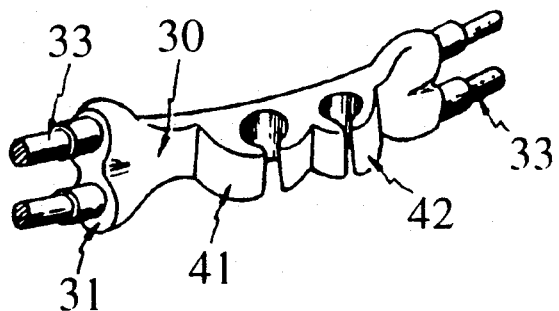
FIGURE.4A
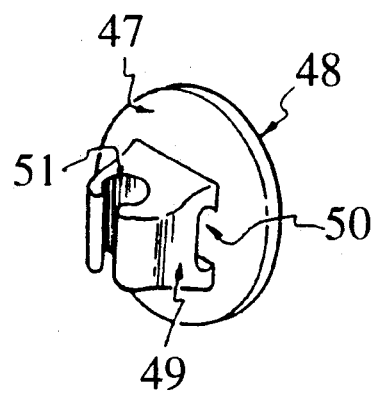
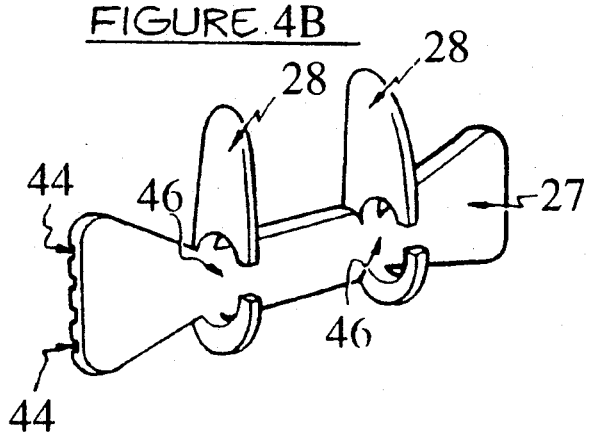
FIGURE.4B
FIGURE.4D
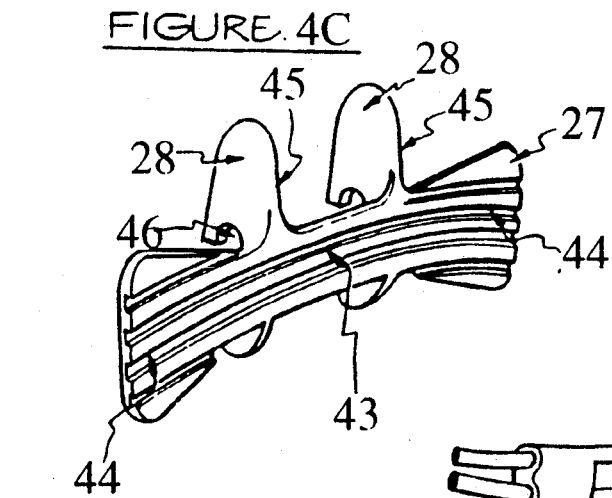
FIGURE.4C
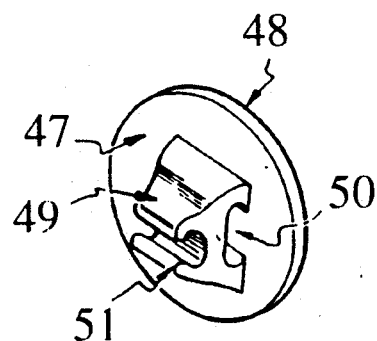
FIGURE.4E
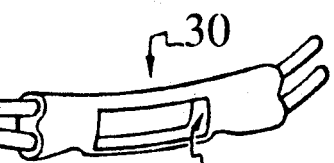
FIGURE.4F
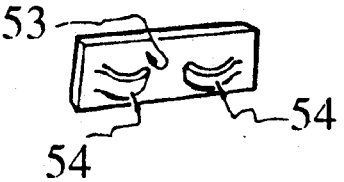
FIGURE.4G

NASAL TUBE HOLDER

The present invention relates to devices for holding tubes especially for gastric feeding tubes once they have been inserted into the nasal passages of patients. Such tubes must be secured to prevent them from falling out or being inadvertently pulled out by a patient. Often such tubes remain in use for quite long periods of time and the means for securing such tubes can therefore cause discomfort to the patient and sometimes, complicating medical conditions.

The most common method of securing nasal tubes for gastric feeding purposes to patients is via the use of adhesive tape. The tape is either placed on top of the nose or placed on the upper lip of the patient where it can cause perspiration and as a result capable of collecting germs. The tubes fastened in this way often become loose and can easily be detached. Moreover such tape, when used over long periods of time causes discomfort to the patient and considerable pain when it is removed. Moreover the tape is continually touched by patients when being worn. The area to which the tape is adhered over a period of weeks often becomes very irritated and sore. Vomitting in such patients is not infrequent necessitating a change of tube and of adhesive tape. If this is not done the tape tends to smell unpleasantly. It should of course be appreciated that gastric feeding tubes are stronger and heavier than oxygen supply tubes and as such any means for holding gastric tubes must be physically stronger than that which might be used for oxygen supply tubes.

There have been other means developed for supplying a patient with gases or fluids through the nose. U.S. Pat. No. 4465067 by Koch et al discloses a holder which is similar to a pair of spectacles. The holder consists of two temple portions designed to rest on the patient's ears which join a front portion substantially at right angles similar to a pair of spectacles. Such a holder would rest on the nose and has a downward extending member which engages the patient's nostril.

The disadvantages of such a holder are clearly apparent. The right angle formed by the front and temple portions justs out from the face providing ample opportunity for the holder to be knocked from the face and possibly injuring the patient. The obstrusive nature of the downward extending member would also be subject to being knocked. In addition the front portion which rests on the nose is likely to cause pressure sores in patients and irritate an area which is not generally padded with subcutaneous fat.

The objectives of the present invention are to provide a comfortable and safe means of securing nasal tubes and particularly gastric feeding tubes to patients. It is the inventors objective to do this by minimizing risk of pressure sores developing, providing a more hygenic means by which tubes can be secured and which facilitates frequent cleaning without patient discomfort. Additionally, it is the inventor's objective to provide a means by which nasal tubes can be secured to patients with highly sensitive skin such as infants and old people.

The nasal tube holder of the present invention comprises a head attachment means associated with a bridging means wherein, when in use, said bridging means traverses the face and is composed of flexible material to conform to facial contours of the patient, said bridging means carrying adjacent to the patient's nose a first nasal connector means.

Preferably the invention includes second nasal tube connector means carried on the bridging means or head attachment means and where two are present, these are located on either side of the first nasal tube connector means. It is a further preferred embodiment that the second nasal tube connector means are movable along the bridging means or the head attachment means so that they can be selectively movable to prevent pressure sores.

It is a further preferred embodiment that said head attachment means comprises loop members designed to encircle a patient's ears. Additionally the head attachment means may comprise a retainer means alone or associated with said loop members. Further, said loop members may be attached to a tube holder body which, when in use, is made of a suitable size and shape to sit under a patient's nose and includes said first nasal tube connector means.

In a still further embodiment, the tube holder body is associated with a backing plate of suitable dimensions to rest under a patient's nose and wherein said backing plate has two wings which when in use sit either side of the patient's nose. The wings may be substantially flush with the surface of the backing plate in contact with the patient's skin. Alternatively the wings are positioned to sit at 90° to the plane of a patient's face. It is additionally preferred that the surface of said backing plate in contact with patient's skin has ventilation means such as a plurality of grooves to facilitate air flow to said skin.

Clearly materials used by the manufacturer are optional. It is however the inventors intention that the holder be as safe and as comfortable as possible. Allergy inducing materials should be avoided and all areas of the holder in contact with the skin should be smooth and relatively soft. In addition, preferably materials which do not promote perspiration should be used. Further materials which have unpleasant smells should be avoided. Brittle materials which are likely to break causing fragments to fall into the patient's mouth or cause scratches should similarly be avoided. Lighter rather than heavier materials should be chosen. Finally, any VELCRO ®, or hook and loop pile fastener used on the head attachment means should be of the non-hairy type to avoid catching and pulling the patient's hair.

Several preferred embodiments of the present invention will hereinafter be described with reference to the accompanying drawings.

BRIEF DESCRIPTION

FIG. 4A shows a perspective view of tube holder body as represented in FIG. 4;

FIG. 4B shows a front perspective view of a backing plate as represented in the embodiment of FIG. 4;

FIG. 4C shows a rear view of the backing plate of FIG. 4B;

FIGS. 4D and 4E show perspective views of the side plates shown in FIG. 4;

FIG. 4F shows a perspective view of a further tube holder body capable of use in the embodiment of FIG. 4;

FIG. 4G represents nasal tube holder connector means plate for use in the tube holder body shown in FIG. 4F.

DETAILED DESCRIPTION

Figure 1:
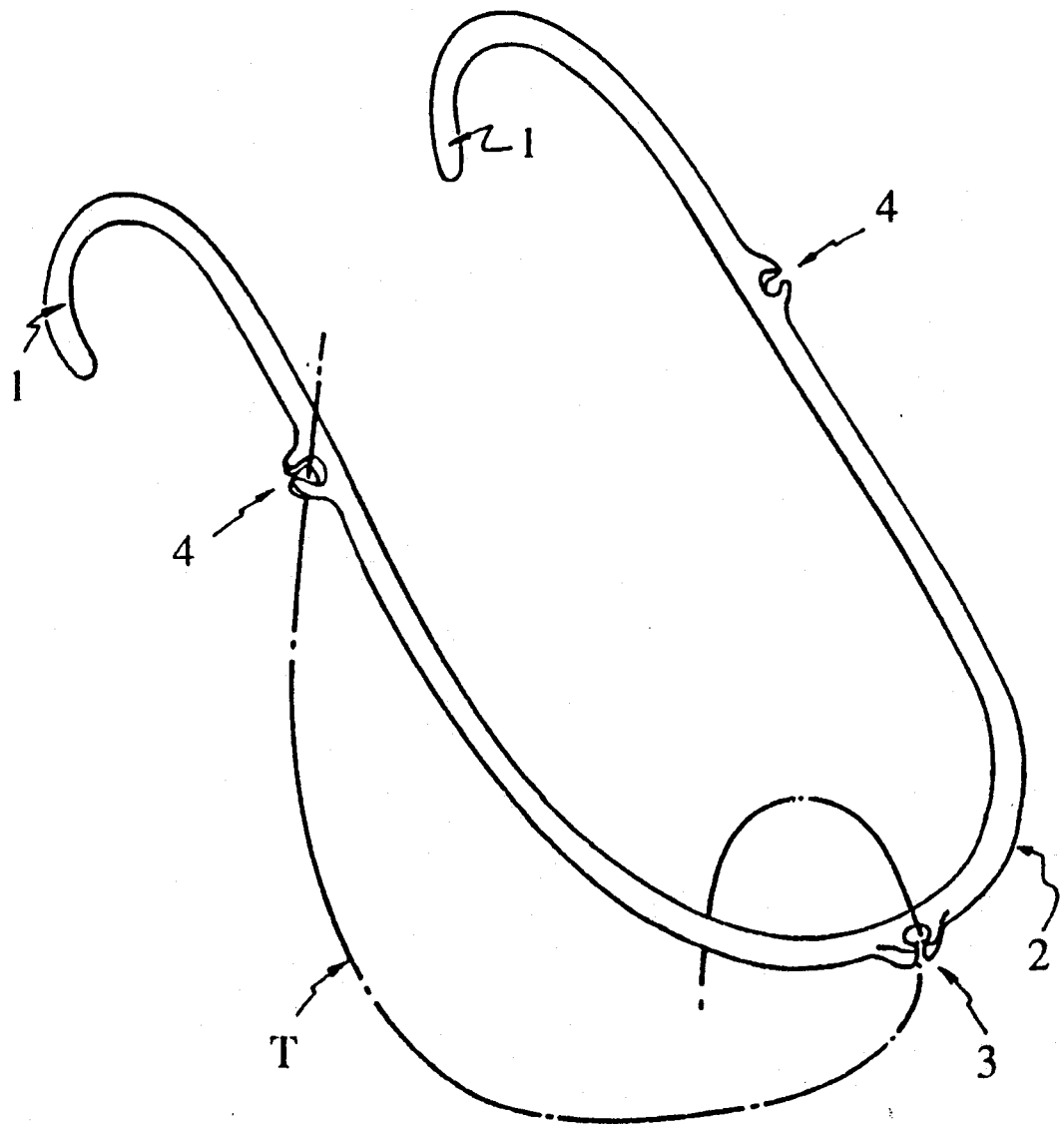
FIG. 1 represents a perspective view of one preferred embodiment of a holder in accordance with the present invention.

FIG. 1 represents a tube holder with head attachment means (1) in the form of hook members designed to rest over and behind the patient's ears, bridging member (2) connecting said hook members and tube connector means (3 and 4) for securing a nasal tube (T) as shown schematically in the drawing.

Figure 1A:
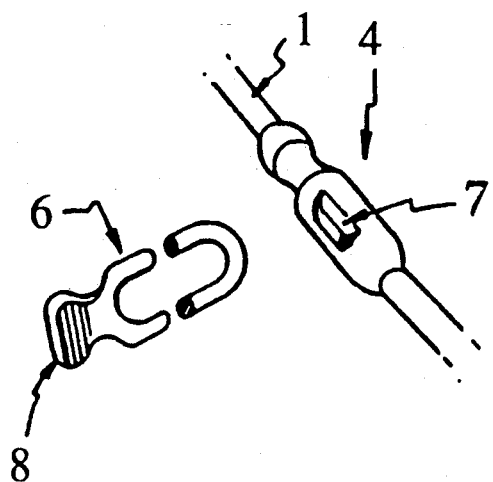
FIGS. 1A, 1B and 1C show perspective views of tube connector means that may be used as variants of the arrangement shown in FIG. 1 or any of the other embodiments disclosed hereinafter.

The embodiment shown in FIG. 1 (or other embodiments) may be produced with a tube connector means (4) in the cheek area (cheek connector means) as shown in FIG. 1A. This connector means (4) may consist of a separate ring retainer member (6) of which one end sits in a groove on the head attachment means (1) and the other end being secured, in use, under a projection (7) on the hook member situated at a suitable distance from said groove. The projection (7) is preferably a rounded protuberance without sharp edges that might cause discomfort to or harm a patient. In one arrangement, the projection (7) may simply be of a size sufficient to require the ring 6 to be forced thereover to be secured thereto. The body of the connector means (4) might include a flat rear plate for engagement against the patient's skin and moreover the body might be movable along the member (1). To facilitate pulling said retainer member (6) into position over the projection (7) a tab-like protrusion (8) can be present on said member (6). The ring retainer member (6) would be most effectively employed if it were constructed of a flexible material. The groove should be sufficiently deep to avoid the ring retainer member projecting inwardly which would be uncomfortable for the patient.

Figure 1B:
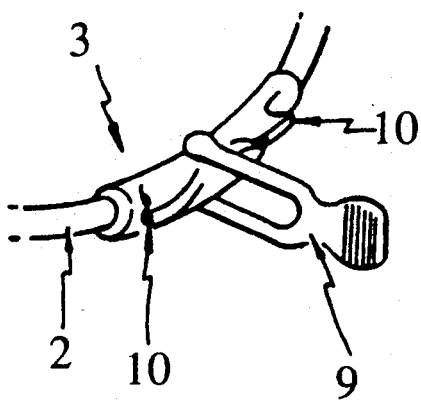

FIG. 1B shows a tube connector means (3) for use in the area of the nose connector means (nasal) which is constructed similarly to the connector means (4) of FIG. 1A. Said means (6) consists of a separate ring retainer member (9) similar to that of FIG. 1A described above. The ring retainer member (9) sits in a groove provided in the bridging member (2). The bridging member (2) having projections (10) similar to that described with reference to FIG. 1A on either side of the groove for the ring retainer member (9) such that a tube may be selectively inserted either in the left or right nostril in a manner similar to that described for FIG. 1 above. Again a flat backing plate might be used.

Figure 1C:
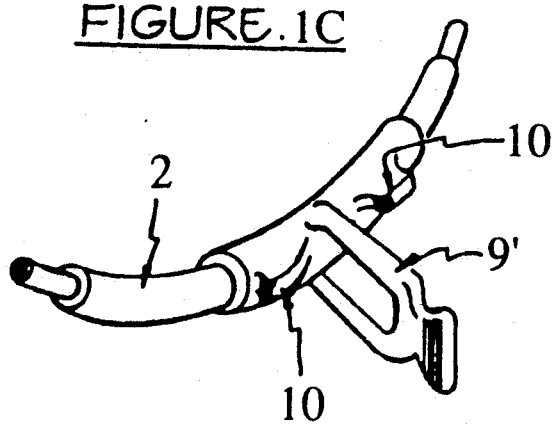

FIG. 1C shows a nasal connector means which functions in the same way as that of FIG. 1B however retainer member (9') instead of being a ring is attached directly, or moulded onto the bridging means (2).

Figure 2:
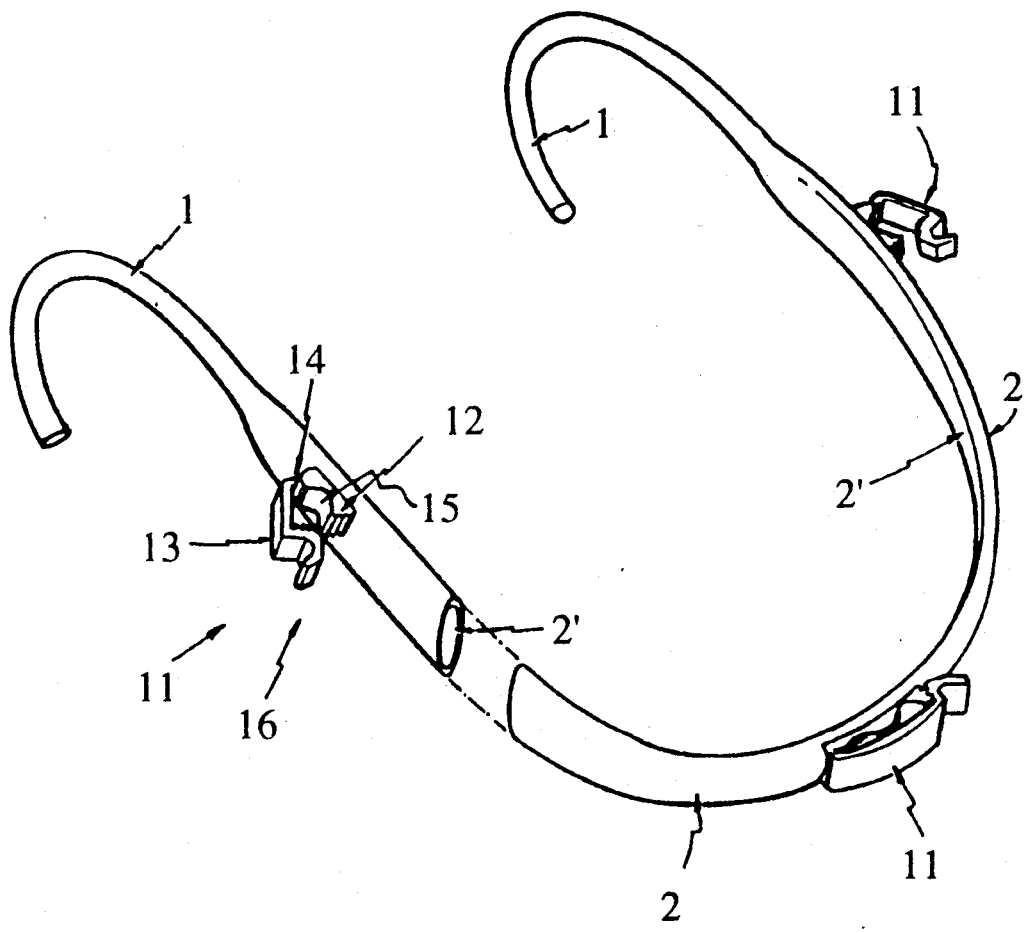
FIG. 2 represents a perspective view of a further preferred embodiment of the invention.

The embodiment illustrated in FIG. 2 shows a bridging member (2) and part of the hook members (1) as being elliptical or flattened in cross-section so that the flat portion (2') is in contact with the face of the patient. This embodiment also shows a ratchet clip tube connector means (11) for both the cheek and nasal zones. The tube connector means (11) comprises a fixed portion (12) connected to the holder and a movable portion (13). The fixed and movable portions (12, 13) are joined by a hinge means (14) and have teeth-like structures at the ends opposite to the hinge means (14). The fixed portion (12) for the cheek zone has one groove (15) of a suitable diameter to accommodate the nasal tube. The fixed portion (12) in the nasal zone may have two grooves (15) as illustrated. If it is desired to minimize the number of mouldings, a connector with two grooves (15) could be used for both the nasal and cheek zones.

The connector means has a tab-like protrusion (16) adjacent to the teeth of the movable portion (13) of the clip to enable the teeth to be opened out to facilitate mating with the teeth of the fixed portion of the clip.

Figure 3:
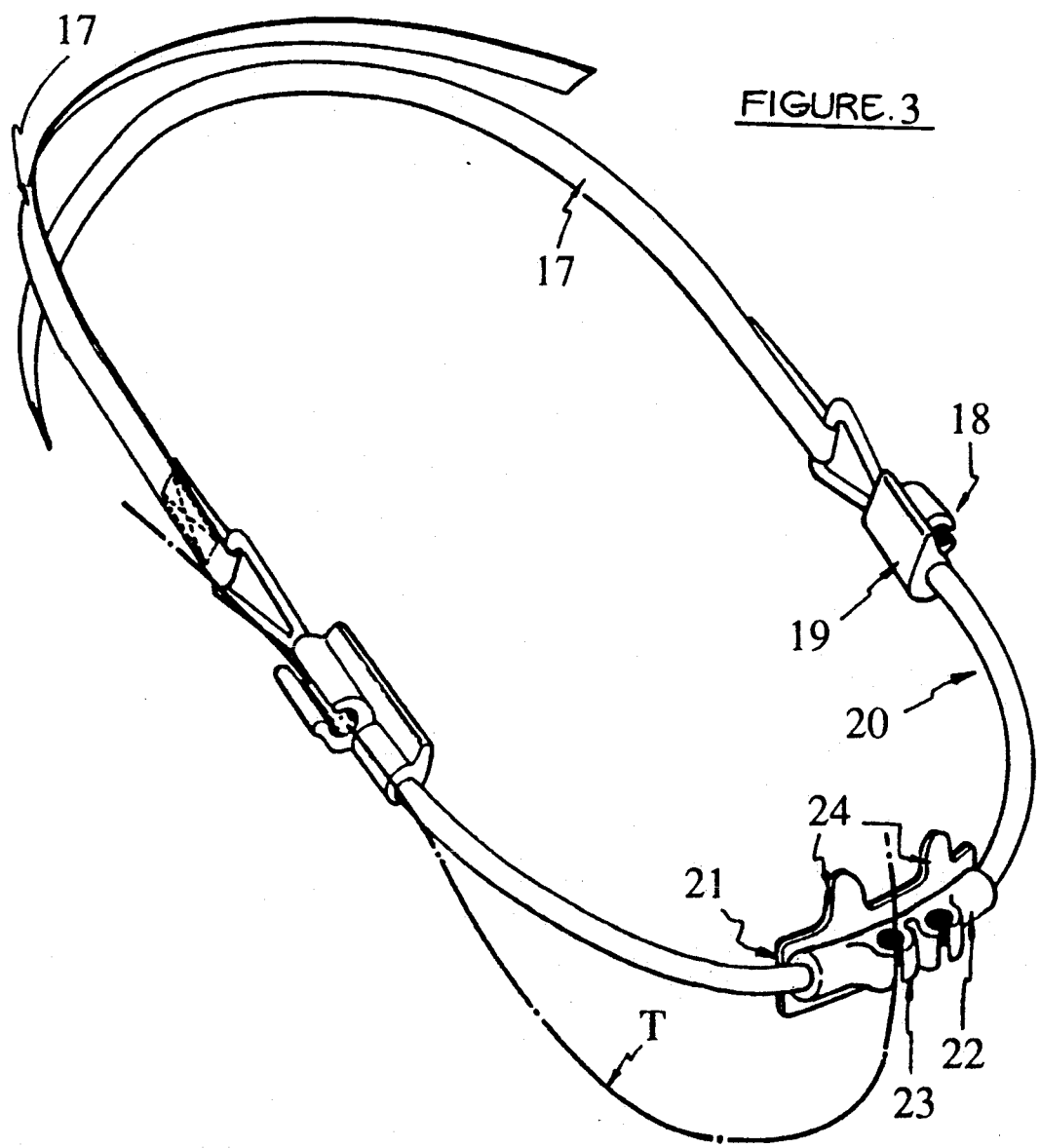
FIG. 3 shows a perspective view of another preferred embodiment of the invention.

FIG. 3 represents a further embodiment of the invention whereby the hook members (1) have been replaced by a strap retainer member (17). Said retainer member advantageously has a means by which the length can be adjusted such as VELCRO ®, or hook and loop pile fastener. The cheek connector means (18) is an integral part of a side plate (19) providing a flat surface for engagement with the patient's face. The cheek connector means (18) illustrated is of a simple clip-like construction similar to that of nasal connector means (3) shown in FIG. 1. The cheek connector means (18) provides for the nasal tube to be secured in such a manner that it runs parallel to the bridging member (20) at the point of its attachment. Moreover, it may be appropriate to arrange the connector means (18) to be movable along member (20). Hook or partial hook members might also be provided to engage a patient's ears. The embodiment also provides for a backing plate (21) onto which a tube holder body (22) may be connected. The body (22) includes the nasal connector means (23) and may be produced from a relatively strong plastics material. The backing plate (21) may be made of a softer and more resilient material. The backing plate also has two wings (24) which, when the arrangement is properly secured on a patient, would sit flat on the face one either side of the nose. Said wings (24) assist in locating the correct position of the nasal connector means and maintaining its position under the nose.

Figure 4:
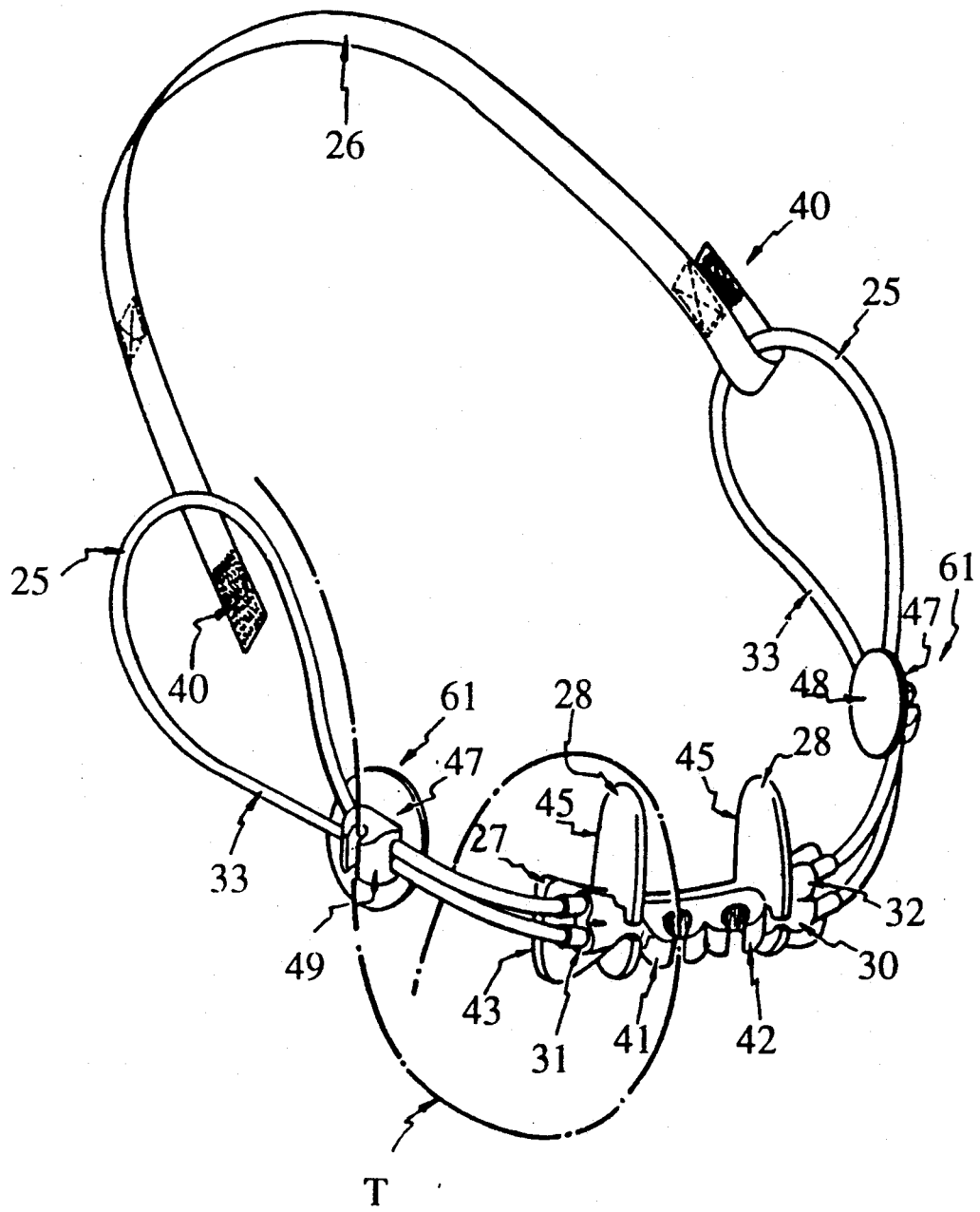
FIG. 4 represents a perspective view of a still further preferred embodiment.

FIG. 4 illustrates a still further embodiment of the present invention. In this embodiment the holder includes a central tube holder body (30) with lateral ends (31, 32). A tube loop (33) is secured to each of the lateral ends (31, 32) of the holder body (30) to form looped ends (25) that are adapted to fit over the ears of a patient. Adjustment of the length of the tube loops (33) to fit patients with different head sizes might be achieved by producing different tube lengths. The tube is conveniently produced from a material similar to the gastric tubes (T) but is of a relatively small diameter Alternatively a separate fastening strap (26) might be employed adapted to connect the loops around the back of a patient's head. The strap 26 might employ adjustable fastening systems such as a velcro fastener means (40) or any other convenient fastening means. The strap (26) may have the effect of slightly lifting the loops (25) from a patient's ears to prevent pressure sores.

The central tube holder body (30) is conveniently produced of a light weight but relatively strong flexible plastics material including a pair of resilient clips (41, 42) at its forward face to enable a tube (T) to be secured thereto. The tube holder body (30) has a backing plate (27) releasably attached thereto. The backing plate (27) may be of a lighter, softer and possibly more resilient plastics material than the body (30). In addition, the rear surface (43) of the plate (27) is essentially flat to minimize any patient discomfort. As shown in FIG. 4C, the rear face (43) of the backing plate (27) has a plurality of shallow grooves (44) formed therein, the purpose of which is to promote air flow to minimize patient discomfort by perspiration build up. The backing plate (27) may include nose engaging members (28) in the form of wings having a rear edge (45) essentially flush with the rear face (43) of the backing plate (27). The wings (28) have no sharp edges and may generally extend perpendicularly from the plate (27) forwardly of the rear face (43) and include a C-shaped opening (46) adapted to provide a releasable clip to fit over the tube holder body (30). The wings (28), when connected to the body (30) fit on either side of the clips (41, 42) to provide a firm and rigid assembly. The provision of the wings (28) extending upwardly as illustrated enable the wings to engage a patient's nose with the clips (41, 42) thereby being held firmly in position. In consequence a firm positioning of the tube (T) is achieved regardless of the probable movement of a patient's head.

It will of course be appreciated that if the backing plate (27) proves to be too heavy for long term use, it might be easily removed. Moreover, it would also be possible to provide the wings (28) such that they have a rear surface generally in the plane of the rear surface (43) of the plate (27) such that inner edges form the engagement means with the patient's nose.

As is further shown in FIG. 4, a pair of cheek area connector means (61) are provided. Each of the connector means (61) comprises a facial engagement plate (47), preferably produced from a firm smooth plastics material. It is advantageous to produce the connector means (61) in a single moulding operation to minimize assembly and production costs. The rear surface (48) of the plate (47) may include a padding material such as a sponge material although it is believed this should not be required. The connector means (61) includes an outer body part (49) that has a through opening (50) adjacent to the plate (47). The opening (50) is of a size sufficient to accommodate two lengths of the tubing forming the loops (33) so that the connector means (61) may be moved therealong for reasons which will be explained hereinafter. Arranged outwardly of the opening (50) is a resilient clip opening (51) which may be vertically arranged as in FIGS. 4 and 4D or generally horizontally arranged as in FIG. 4E. As is shown the tube (T) passes from the patient's nose through the central clip 41 (or 42) to one of the side clips (61) to ensure that the tube (T) does not hang down in front of the patient. This arrangement minimizes the risk of a patient pulling the tube out involuntarily. Provision for the side clips (61) being movable along the tube loops (33) provides the option of positioning the clips on a patient's face at a location where it is unlikely to press against a bone or the like and provide discomfort to the patient. Moveover, if the clips (31) are located in a fixed position, it is likely over long term use, that pressure sores will result. Movement of the clips (31) periodically will prevent such sores developing. Finally, the clips (31) on either side of the face, can be separately adjusted depending on which side the patient is lying. The arrangement thus described and illustrated in FIGS. 4, and 4A to 4E provide a relatively comfortable nasal tube holder, particularly for gastric feeding purposes, which is adapted for use over relatively long periods, the holder being simply produced from a minimum of parts and using a minimum of plastic mouldings.

The item may be reused or be disposable after use by any particular patient.

FIGS. 4F and 4G illustrate a possible modification of the arrangement shown in FIGS. 4 and 4A to 4E. In this embodiment the central tube holder body (30) may be formed with a through opening or blind recess (52) enabling a separate retainer clip plate (53) to be secured therein. The clip plate (53) may include resilient clip elements (54) moulded to the plate with an end free enabling a tube (T) to be clipped therethrough. The body (30) may be adapted to receive a backing plate as described aforesaid with reference to FIG. 4, or not, as desired. Moreover the body (30) might be produced from relatively soft resilient plastic with the clip plate (53) produced from a stronger plastic.

Figure 5:
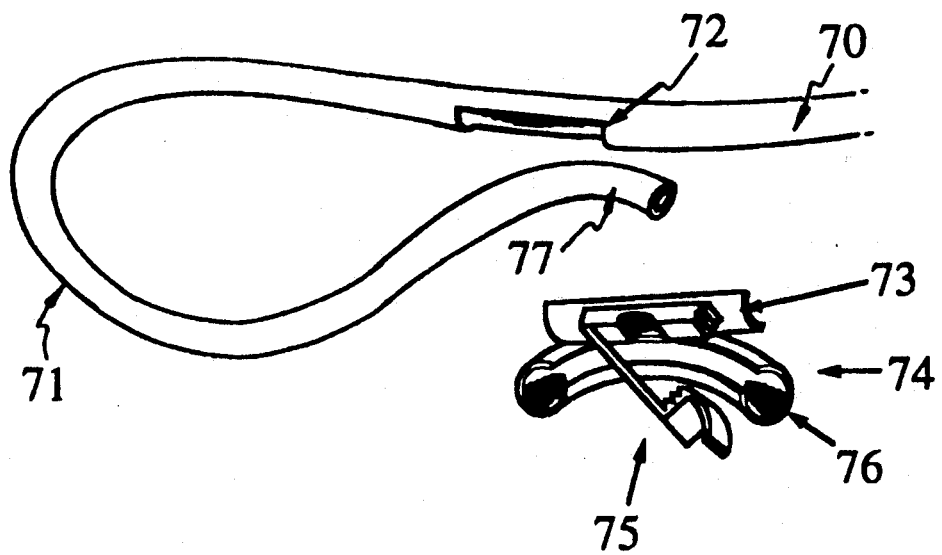
FIG. 5 is a perspective view of a further possible variant capable of use in the performance of the present invention.

FIG. 5 illustrates a further alternative embodiment that might be employed. The drawing illustrates a portion of a holder adapted for attachment to a patient's ears, the remainder of the holder comprising a bridging section and a second ear attachment portion as illustrated. The holder includes a tube element (70) formed into an ear engaging loop (71). The tube element (70) includes a zone (72) prepared to have a portion (73) of a tube connector means (74) bonded or fastened thereto. The portion (73) includes a tube engaging clip (75) constructed in a manner previously described in relation to FIG. 2. Below the portion (73), a partial tubular section (76) is secured so that the end (77) of the tube element (70) can be passed therethrough. The portion 76 enables the tube element (70) to be pulled therethrough to adjust its length and be retained in the adjusted length. It will of course be apparent that any form of nasal tube holder means as described previously with reference to the other embodiments may be used on the bridging section of this embodiment.

I claim:

1. A nasal tube holder comprising:
   a structural member, adapted to be positioned between a patient's nose and mouth.
   a first nasal tube connector means for connecting a nasal tube to said structural member, said first nasal tube connector means including a first outwardly facing clip means for releasably holding at least one nasal tube, said structural member having a substantially flat surface for engagement with the patient's skin between the patient's nose and mouth;
   elongated flexible members extending from opposed ends of said first nasal tube connector means, each of said elongated flexible members terminating in a closed loop adapted to surround a patient's ear; and
   at least one second nasal tube connector means for connecting a nasal tube, said second nasal tube connector means being attached to one of said elongated flexible members for selective movement therealong, said second nasal tube connector means including a substantially flat surface for contacting against the patient's skin and a second outwardly facing clip means for releasably holding said nasal tube.

2. A nasal tube holder according to claim 1 wherein each of said elongated flexible members comprise a single element having two free ends joined to said structural member.

3. A nasal tube holder according to claim 2 wherein said second nasal tube connector means is slidably connected to adjacent lengths of said single element forming said elongated flexible member.

4. A nasal tube holder according to claim 1 further including strap means for connecting one of said closed loops to the other of said closed loops, said strap means having a first strap end, said first strap end of said strap means including releasable fastening means for releasable connection with one of said closed loops.

5. A nasal tube holder according to claim 4 wherein said releasable fastening means includes adjustment means for enabling said closed loops to be lifted off a rear zone of the patients ears.

6. A nasal tube holder according to claim 1 wherein said substantially flat surface of said structural member includes a peripheral edge and at least one groove having a first end, said groove formed into said substantially flat surface with said first end of said groove terminating at a peripheral edge of a substantially flat surface.

7. A nasal tube holder according to claim 1 wherein said first clip means of said first nasal tube connector means comprises two clip devices, each of said clip devices being adapted to releaseably hold a nasal tube.

8. A nasal tube holder according to claim 1 wherein said first nasal tube connector means includes a pair of spaced and upwardly directed projections, each of said projections adapted, in use, to be located on opposed sides of the patient's nose.

9. A nasal tube holder according to claim 1 wherein said second clip means of said second nasal tube connector means includes means for connecting a nasal tube to lie parallel to said elongated flexible member adjacent to said second nasal tube connector means.

10. A nasal tube holder according to claim 1 wherein said second clip means of said second nasal tube connector means includes means for connecting a nasal tube to lie at 90° to said elongated flexible member adjacent to said second nasal tube connector means.

11. A nasal tube holder according to claim 1 wherein said structural member further comprises first and second parts, said first part carrying said substantially flat surface and said second part carrying said first clip means of said first nasal tube connector means, said first and second parts being releasably engageable with each other.

* * * * *